US006333317B1

(12) United States Patent
Lee et al.

(10) Patent No.: US 6,333,317 B1
(45) Date of Patent: Dec. 25, 2001

(54) REGULATION OF AMYLOID PRECURSOR PROTEIN (APP) EXPRESSION BY ADMINISTRATION OF AN ESTROGENIC COMPOUND

(75) Inventors: Robert K. K. Lee; Richard J. Wurtman, both of Boston, MA (US)

(73) Assignee: Massachusettes Institute of Technology

( * ) Notice: Subject to any disclaimer, the term of this patent is extended or adjusted under 35 U.S.C. 154(b) by 0 days.

(21) Appl. No.: 09/049,198

(22) Filed: Mar. 27, 1998

Related U.S. Application Data
(60) Provisional application No. 60/042,858, filed on Mar. 28, 1997, now abandoned.

(51) Int. Cl.[7] .................................................. A01N 37/36
(52) U.S. Cl. ......................... 514/162; 514/178; 514/182; 552/625
(58) Field of Search .................................. 514/162, 178, 514/182; 552/625

(56) References Cited

U.S. PATENT DOCUMENTS

| 4,791,099 | 12/1988 | Aroonsakul ............................... 514/2 |
| 5,547,841 | 8/1996 | Marotta et al. ........................... 435/6 |
| 5,554,601 | 9/1996 | Simpkins et al. ..................... 514/182 |
| 5,556,847 | 9/1996 | Johnson ................................ 514/178 |
| 5,643,726 | 7/1997 | Tanzi et al. .............................. 435/6 |
| 5,719,137 | 2/1998 | Washburn et al. ................... 514/182 |

OTHER PUBLICATIONS

Birge, "Is There a Role for Estogen Replacement Therapy in the Prevention and Treatment of Dementia," *J. American Geriatrics Soc.*, 44(7), 865–870 (Jul. 1996).*
Paganini–Hill et al., "Estrogen Deficiency and Risk of Alzheimer's Disease in Women." *American J. Epidemiology*, 140(3), 256–261 (1994).*
Jaffe et al., "Estrogen Regulates Metabolism of Alzheimer Amyloid β Precursor Protein," *J. Biological Chemistry*, 269(18), 13065–13068 (May 6, 1994).*
Cordell, β–Amyloid Formation as a Potential Therapeutic Target for Alzheimer's Disease, *Annual Reviews Pharmacology Toxicology*, 34, 69–89 (1994).*
Selkoe, "Normal and Abnormal Biology of the β–Amyloid Precurssor Protein," *Annual Reviews in Neuroscience*, 17, 489–517 (1994).*
Nitsch et al., "Release of Alzheimer Amyloid Precursor Derivatives Stimulated by Activation of Muscarinic Acetylcholine Receptors," *Science*, 258, 304–307 (Oct. 9, 1992).*
Wolf et al., "Muscarinic Regulation of Alzheimer's Disease Amyloid Precursor Protein Secretion and Amyloid β–Protein Production in Human Neuronal NT2N Cells," *J. Biological Chemistry*, 270(9), 4916–4922 (Mar. 3, 1995).*

Buxbaum et al. (I), "Calciuim Regulates Processing of the Alzheimer Amyloid Protein Precursor in a Protein Kinase C–Independent Manner," *Proc. National Academy Sciences USA*, 91(10), 4489–4493 (May 10, 1994).*
Lee et al. (I), "Amyloid Precursor Protein Processing Is Stimulated by Metabotrophic Glutamate Receptors," *Proc. National Academy Sciences USA*, 92, 8083–8087 (Aug. 1995).*
Ulus et al., "Metabotropic Glutamate Receptor Agonists Increase Release of Soluble Amyloid Precursor Protein Derivatives from Rat Brain Cortical and Hippocampal Slices," *J. of Pharmacology and Experimental Therapeutics*, 281(1), 149–154 (1997).*
Efthimiopoulos et al., "Intracellular Cyclic AMP Inhibits Constitutive and Phorbol Ester–Stimulated Secretory Cleavage of Amyloid Precursor Protein," *J. Neurochemistry*, 67, 872–875 (1996).*
Lee et al. (II), "Metabotropic Glutamate Receptors Increase Amyloid Precursor Protein Processing in Astrocytes; Inhibition by Cyclic AMP," *J. Neurochemistry*, 68, 1830–1835 (1997).*
Yankner et al., "Neurotoxicity of a Fragment of the Amyloid Precursor Associated with Alzheimer's Disease," *Science*, 245, 417–420 (Jul. 28, 1989).*
Kozlowski et al., "The Neurotoxic Carboxy–Terminal Fragment of the Alzheimer Amyloid Precursor Binds Specifically to a Neuronal Cell Surface Molecule: pH Dependence of the Neurotoxicity and the Binding," *J. Neuroscience*, 12(5), 1679–1687 (May 1992).*
Maruyama et al., "Formation of Amyloid–Like Fibrils in COS Cells Overexpressing Part of the Alzheimer Amyloid Protein Precursor," *Nature*, 347, 566–569 (Oct. 11, 1990).*

(List continued on next page.)

*Primary Examiner*—Gary Geist
*Assistant Examiner*—L. E. Crane
(74) *Attorney, Agent, or Firm*—Gilberto M. Villacorta; Corinne M. Pouliquen; Pepper Hamilton, L.L.P.

(57) ABSTRACT

It has been discovered that lipophilic hormones that interact with cytosolic or nuclear receptors regulate APP expression and synthesis, through modification of APP mRNA stability and/or regulation of APP gene transcription and translation activities. These studies demonstrate that the treatment of brain cells with estrone or 17β-estradiol results in a reduction in the level of APP holoprotein expression, without a concomitant change in the total level of cell protein. The reduction in the level of APP holoprotein caused by estrone or 17β-estradiol is also expected to reduce the production of neurotoxic APP fragments. In as much as estrogen deficiency in postmenopausal women is associated with a higher incidence of Alzheimer's disease, this discovery opens the possibility that estrogen therapy may prevent some of the neurodegenerative and cognitive changes associated with Alzheimer's disease, aging and other disease conditions associated with such neurodegenerative and cognitive decline.

13 Claims, 3 Drawing Sheets

OTHER PUBLICATIONS

Hsiao et al., "Age–Related CNS Disorder and Early Death in Transgenic FVB/N Mice Overexpressing Alzheimer Amyloid Precursor Proteins," Neuron, 15(5), 1203–1218 (Nov. 1995).*

Moran et al., "Age–Related Learning Deficits in Transgenic Mice Expressing the 751–Amino Acid Isoform of Human β–Amyloid Precursor Protein," Proc. National Academy Sciences USA, 92(12), 5341–5345 (Jun. 6, 1995).*

Golde et al., "Expression of β–Amyloid Protein Precursor mRNAs: Recognition of a Novel Alternative Splicing Form and Quantitation in Alzheimer's Disease Using PCR," Neuron, 4(2), 253–267 (Feb. 1990).*

Neve et al., "Expression of the Alzheimer Amyloid Precursor Gene Transcripts in the Human Brain," Neuron, 1, 669–677 (Oct. 1988).*

Anderson et al., "Differential Brain Expression of the Alzheimer's Amyloid Precursor Protein," The EMBO Journal, 8(12), 3627–2632 (Dec. 1,, 1989).*

Nordstedt et al., "Alzheimer β/A4 Amyloid Precursor Protein in Human Brain: Aging–Associated Increases in Holoprotein and in a Proteolytic Fragment," Proc. National Academy Sciences USA, 88(20), 8910–8914 (Oct. 15, 1991).*

McGeer et al., "Anti–Inflammatory Drugs and Alzheimer Disease," The Lancet, 335, 1037 (Apr. 28, 1990).*

Andersen et al., "Do Nonsteroidal Anti–Inflammatory Drugs Decrease the Risk for Alzheimer's Disease?" Neurobiology, 45(8), 1441–1445 (Aug. 1995).*

Rich et al., "Nonsteroidal Anti–Inflammatory Drugs in Alzheimer's Disease," Neurobiology, 45(1), 45–51 (Jan. 1995).*

Lindsay (ed.), "The Canadian Study of Health and Aging: Risk Factors for Alzheimer's Disease in Canada," Neurobiology, 44(11), 2073–2080 (Nov. 1994).*

Rogers et al., "Clinical Trial of Indomethacin in Alzheimer's Disease," Neurobiology, 43(8), 1609–1611 (Aug. 1993).*

Siman et al., "Expression of β–Amyloid Precursor Protein in Reactive Astrocytes Following Neuronal Damage," Neuron, 3, 275–283 (Sep. 1989).*

Banati et al., "Glial Expression of the β–Amyloid Precursor Protein (APP) in Global Ischemia," J. Cerebral Blood Flow and Metabolism, 15(4), 647–654 (Jul. 1995).*

Brun et al., "Synapse Loss and Gliosis in the Molecular Layer of the Cerebral Cortex in Alzheimer's Disease and in Frontal Lobe Degeneration," Neurodegeneration, 4, 171–177 (1995).*

Caporaso et al.(I), "Protein Phosphorylation Regulates Secretion of Alzheimer β/A4 Amyloid precursor Protein," Proc. National Academy Sciences USA, 89, 3055–3059 (Apr. 1992).*

Caporaso et al.(II), "Chloroquine Inhibits Intracellular Degradation But Not Secretion of Alzheimer β/A4 Amyloid Precursor Protein," Proc. National Academy Sciences USA, 89, 2252–2256 (Mar. 1992).*

Buxbaum et al. (II), "Cholinergic Agonists and Interleukin 1 Regulate Processing and Secretion of the Alzheimer β/A4 Amyloid Protein Precursor," Proc. National Academy Sciences USA, 89, 10075–10078 (Nov. 1992).*

Lee et al. (III), "Stimulation of Amyloid Precursor Protein Synthesis by Adrenergic Receptors Coupled to cAMP Formation," Proc. National Academy Sciences USA, 94, 5422–5426 (May 1997).*

Lee et al. (IV), "Prostaglandin $E_2$ Stimulates Overexpression of Amyloid Precursor Protein in Cultured Astrocytes Inhibition by Cyclosporin A," J. Neurochemistry, 69(Supplement), p. S103 (1997); See Abstract B.*

Tomlinson, "Ageing and the Dementias," Ch. 20 in Greenfield's Neuropathology, Fifth Edition, Adams et al. (eds.), Oxford University Press, New York, NY, 1992, pp. 1284–1410.*

Henderson et al., "Estrogen Replacement Therapy in Older Women," Arch. Neurology, 51, 896–900 (Sep. 1994).*

Lagrange et al. "An Estrogen Receptor that Nongenomically Uncouples G–Protein Coupled Receptors," Abstract No. 152.17, Society for Neuroscience, 26th Annual Meeting, Washington, D.C., Nov. 16, 1996, vol. 22, Part 1, p. 378.*

LeBlanc et al. (I), "Amyloid Precursor Protein Metabolism in Primary Cell Cultures of Neurons, Astrocytes, and Microglia," J. Neurochemistry, 66, 2300–2310 (1996).*

LeBlanc et al. (II), "Processing of Amyloid Precursor Protein in Human Primary Neuron and Astrocyte Cultures," J. Neurochemistry, 68(3), 1183–1190 (1997).*

Mills et al., "Phorbol Esters But Not the Cholinergic Agonists Oxotremorine–M and Carbachol Increase Release of the Amyloid Precursor Protein in Cultured Rat Cortical Neurons," J. Neurochemistry, 67(4), 1511–1518 (1996).*

McCarthy et al., "Preparation of Separate Astroglial and Oligodendrogial Cell Cultures From Rat Cerebral Tissues," J. Cell Biology, 85(3), 890–902 (Jun. 1980).*

\* cited by examiner

REGULATION OF AMYLOID PRECURSOR PROTEIN (APP) EXPRESSION BY ADMINISTRATION OF AN ESTROGENIC COMPOUND

RELATED APPLICATIONS

The present application claims the benefit of the priority date of U.S. Provisional Application 60/042,858, filed Mar. 28, 1997, now abandoned.

STATEMENT OF FEDERAL SUPPORT

The present invention is made in whole or in part with financial support from the Federal Government under grant NIH #MH-28783. The Federal Government may have rights in the invention.

FIELD OF THE INVENTION

The present invention relates to compositions and methods for the treatment of various neurological diseases and neurodegenerative disorders associated with aging, particularly those affected by an overabundance of Amyloid Precursor Protein (APP). In particular, this invention relates to the APP holoprotein synthesis and the effect of lipophilic compounds on regulating the expression of this protein. In particular, it has been discovered that certain neurodegenerative or cognitive changes are associated with developing an imbalance in the serum levels of endogenous, gynecologically relevant substances, including certain neurotransmitters, neurotransmitter substrates or hormones. It has also been found that the level of APP holoprotein is reduced by lipophilic estrogenic compounds in brain cells, and that this reduction is expected to reduce the neurotoxicity or neurodegeneration associated with APP over expression.

BACKGROUND OF THE INVENTION

Alzheimer's Disease (AD) is the most common neurodegenerative disorder of aging, and is characterized by progressive dementia and personality dysfunction. The abnormal accumulation of amyloid plaques in the vicinity of degenerating neurons and reactive astrocytes is a pathological characteristic of AD.

Several lines of studies suggest that postmenopausal women with lower levels of endogenous estrogen may be predisposed to the development of AD. Studies in experimental animal models provide a convincing rational for the role of estrogen replacement therapy and prevention of dementia. See, for example, Birge, *J. Am. Geriatric. Soc.* 44, 865, (1996). These studies suggest that estrogen deficiency in postmenopausal women apparently increases their susceptibility to the neurodegenerative changes of aging and AD, and that this risk can be decreased by estrogenic replacement therapy. Peganini et al. *Am. J. Epidemiol*, 140, 256 (1994). Estrogen treatment of cell culture reportedly promotes non-amyloidogenic APP processing and soluble APP (APPs) secretion. Jaffe et al.,*J. Biol. Chem.* 269, 13065 (1994).

APP processing is regulated by neurotransmitters and synaptic activity. Amyloid plaques in AD accumulate near dystrophic neurons and reactive astrocytes. Cordell, *Annu. Rev. Pharmacol. Toxicol.* 34, 69 (1994); Selkoe, Annu. Rev. Neurosci. 17, 489 (1994). The activation of neurotransmitter receptors, which are coupled to phosphotidylinositol (PI) hydrolysis or to protein kinase C (PKC) activation, can promote APP metabolism and decrease amyloid formation. Nitsch, et al., *Science* 258, 304 (1992); Wolf et al., *J. Biol. Chem.* 270, 4916 (1995); Buxbaum et al., *Proc. Natl. Acad. Sci. U.S.A.* 91, 4489 (1994); Lee, et al., Ibid., 92, 8083 (1995); Ulus and Wurtman, *J. Pharm. Exp. Ther.*, 281,149 (1997); Lee et al., *Proc. Natl. Acad. Sci. U.S.A.* 92, 8083 (1995). Activation of neurotransmitters coupled to cAMP production suppresses both constitutive and PKC/PI-stimulated APPs secretion in astroglioma cells and in primary astrocytes. Eftimiopoulos et al., *J. Neurochem.*, 67, 872 (1996); Lee et al., *J. Neurochem.*, 68,1830 (1997). The drastic alterations in neurotransmitter levels and second messenger signaling created by neurodegeneration and synapse loss in AD may disrupt APP processing in ways that promote the accumulation of amyloidogenic or neurotoxic APP fragments.

Additionally, the loss of various neurotransmitters in AD may increase cellular levels of APP holoprotein containing amyloidogenic or neurotoxic peptides due to a decrease in proper APP metabolism. Yankner et al., *Science*, 245, 417 (1989); M. R. Kozlowski, A. Spanoyannnis, S. P. Manly, S. A. Fidel, R. L. Neve, *J. Neurosci*, 12, 1679 (1992).

Increased APP production in Down's syndrome is associated with a high incidence of AD at an early age due to the extra copy of the APP gene. Over expression of APP in cell cultures and in transgenic mice is also associated with neurodegeneration and age-related cognitive deficits, suggesting that over expression of APP could contribute to the neuropathology of AD. Maruyama, et al., *Nature*, 347, 566 (1990); Hsiao et al., *Neuron* 15, 1203–1218 (1995); Moran, et al., *Proc. Natl. Acad Sci. U.S.A.* 92, 5341 (1995).

Several APP isoforms, ranging in size from 695–770 amino acids, are derived by differential splicing of a primary transcript of the three major APP isoforms, APP-695 is predominantly expressed in neurons; APP-751 and APP-770, which harbor an additional Kunitz-type protease inhibitor (KPI) insert at the N-terminus, are predominantly expressed in astrocytes and appear to be increased in AD brain. Golde, S. et al., *Neuron* 4, 253 (1990); Neve, et al.,Ibid., 1, 669 (1990); Anderson et al., EMBO J. 8, 3627 (1989); Nordstedt et al., *Proc. Natl. Acad. Sci. U.S.A.* 88, 8910 (1991). The decreased amounts of APP-695 in post-mortem AD brains may be due to neuronal loss. The increase in KPI-containing APP isoforms in AD and in regions surrounding senile plaques raises the possibility that APP overexpression in astrocytes contributes to AD neuropathology.

Several lines of studies have indicated an apparently low incidence of Alzheimer's Disease in rheumatoid arthritis patients. These studies propose the possibility that anti-inflammatory therapy with NSAIDs (non-steroidal anti-inflammatory drugs) confers some protection against AD. See, e.g., McGeer, et al., *Lancet*, 335, 1037 (1990); Andersen, et al., *Neurology*, 45, 1441 (1995); Rich, et al. Neurology, 45, 51 (1995); Lindsay, et al., *Neurology*, 44, 2073 (1994); Rogers, et al., *Neurology*, 43, 1609 (1993). These studies suggest that the administration of a non-steroidal anti-inflammatory drug may reduce the onset of dementia in Alzheimer's patients. However, none of these studies discloses or suggests that the administration of NSDAs prevents the overproduction of APP.

Persistent and rapid elevations in APP immunoreactivity have been observed in GFAP-positive astrocytes following brain injury. Siman et al.,*J. Neurosci.*, 3, 275 (1989); Banati and Kreutzberg, *J. Cereb. Blood Flow Metab.*, 12, 257 (1995). In the AD brain, the loss of synapses is associated with an increase in the number of GFAP-positive astrocytes (Brun et al., *Neurodegeneration*, 4, 171 (1995), and increases in KPI containing APP mRNA in the frontal cortex have also been attributed to the astrocytic response during neuronal damage (Golde et al., *Neuron*, 4, 253 (1990). It seems that the loss of synapses and neurons in AD might initiate a pathological cascade that includes APP overexpression by reactive astrocytes.

In U.S. Pat. No. 5,385,915, Buxbaum et al. describe methods and compositions for affecting APP processing by the administration of agents that regulate protein phosphorylation, namely agents that regulate kinases or phosphatases. The modulation of APP processing leads, in turn, to the regulation of the production of β/A$_4$ peptide, a peptide that accumulates in amyloidogenic plaques. See, e.g., col. 6, lines 8–10. Hence, Buxbaum et al. teach that one's objective should focus on the search for agents that alter the metabolism of APP.

However, Buxbaum et al. make no mention, teaching, or suggestion that the step preceding the processing of APP, that is, the expression, production, or formation of APP, itself, can be at all affected by select groups of substances. Indeed, as Buxbaum et al. state (at col. 21, lines 7–9), "the effects observed are attributable to changes in APP metabolism rather than APP transcription (emphasis added)." Consistent with this notion, the claims of Buxbaum et al. are drawn to a method of regulating phosphorylation of proteins that control the processing of APP.

Similarly, in U.S. Pat. No. 5,242,932, Gandy et al. disclose and claim a method of modulating or affecting the intracellular trafficking and processing of APP in the mammalian cell.

For additional background information on the processing of APP, release of APP derivatives, or the processing, degradation and secretion of β/A$_4$ APP, the interested reader is referred to the following publications: Nitsch, et al. *Science*, 258, 304 (1992); Lee, et al., *Proc. Nat'l. Acad. Sci. USA*, 92, 8083 (1995); Caporaso, et al. *Proc. Nat'l. Acad. Sci. U.S.A*, 89, 3055 (1992); Caporaso, et al. *Proc. Nat'l. Acad. Sci. U.S.A*, 89, 225 (1992); and Buxbaum, et al. *Proc. Nat'l. Acad. Sci. U.S.A*, 89, 10075 (1992).

In contrast to the above studies, the present invention, as disclosed herein, concerns the expression, formation, or synthesis of APP. The present inventors have previously discovered that cAMP elevations caused by activation of neurotransmitter receptors increased APP mRNA and holoprotein production in astrocytes. Lee et al.,et al. *Proc. Nat'l. Acad. Sci. U.S.A*, 94, 5422 (1997). The present inventors have also shown that activation of prostaglandin E$_2$ (PG E$_2$) receptors coupled to increased cAMP formation also stimulates the synthesis of APP mRNA and holoprotein and that this effect can be mediated by cAMP-dependent protein kinases, and can be inhibited by various substances, including immunosuppressants and ion-channel modulators. Lee et al., *J. Neurochem.* (supp) 69, S103B (1997). As described herein, the present inventors have now shown that APP expression can also be regulated by lipophilic hormones that interact with cytosolic or nuclear receptors.

Estrogen receptors within the brain have a regional distribution strikingly similar to that characteristics of AD-type brain pathology, Thomlinson, B. E.(1992): In *Greenfield's neuropathology* (Adams, J. H. and Duchen L. W. eds)pp 1284–1410 Oxford University Press. In addition recent findings suggest that estrogen replacement therapy my be protective against AD, Henderson, et al.,*Arch neurol* (1994). In order to test the hypothesis that gonadal esteroids might play a role in regulating APP metabolism, Jaffe, et al., *J. Biol. chem.*269, 13065 (1994) investigated the possible effect of estrogen on the metabolism of Alzheimer's amyloid precursor protein. Using a cell line that contains high level of estrogen receptors, these authors found that the treatment with 17β-estradiol is associated with the accumulation of APPs in the medium, indicative of non-amyloidogenic processing. However, these authors found no changes in the levels of intracellular immature or mature APP holoproteins, suggesting that estrogen may increase the secretory metabolism of APP.

Additionally, Hsiao et al., *Neuron*, 15, 1203 (1995), disclose that age-related central nervous system (CNS) disorder and early death in mice were due to over expression of APP, rather than amyloid, with increasing level of intracellular APP, indicating that some deleterious processes related to APP over expression are dissociated from formation of arnyloid.

Previously, it has been shown that neurotrophic effect of estrogen may be through uncoupling signal transduction mechanism of certain receptors linked to G-proteins. Lagrange, et al., *Soc. Neursci. Abstr.* 22, 378, (1996). Additionally, the present inventors have discovered that G-protein coupled receptors which stimulate cAMP formation or PI hydrolysis can accelerate the synthesis and metabolism of APP respectively.

This invention, as disclosed herein, demonstrates for the first time that lipophilic compounds such as estrogen affects the synthesis of the APP holoprotein. The present invention also contemplates and provides an assay for identifying or screening potential drugs that can inhibit the excessive production of neurotoxic APP. For example, such an assay may utilize a tissue or cell culture comprising brain cells, as described herein.

These and other objects of the invention will be evident to those of ordinary skill from a consideration of the discussions and descriptions provided in this specification, including the detailed description of the preferred embodiments.

SUMMARY OF THE INVENTION

It has now been discovered that APP expression can be regulated by lipophilic hormones that interact with cytosolic or nuclear receptors. By contrast to cell-surface receptors that activate second messengers, receptor estrogen complexes typically accumulate in the nucleus where they modify mRNA stability or DNA transcription. Thus, these substances can be used to prevent APP overexpression in brain cells.

What is more, it has been shown that lipophilic estrogenic compounds, such as estrone or 17β-estradiol, inhibit an abnormal increase in the level of APP synthesis (mRNA and cell-associated protein). We have shown that prolonged activation of receptors that are coupled to increased cAMP formation in cortical astrocytes up regulates both APP mRNA levels and APP holoprotein bearing the KPI insert. It has further been discovered that such overproduction, which is shown can result from the body's response to brain injury or trauma, can be inhibited by certain substances, including lipophilic hormones that interact with cytosolic or nuclear receptors.

An object of this invention is to provide compositions and methods for modulating expression, production, or formation of amyloid precursor protein (APP) in a subject comprising administering to the subject an effective amount of a lipophilic hormone, an analog of a lipophilic hormone, a substance that is a ligand, an agonist, or an antagonist of a receptor that is coupled to a lipophilic hormone, and a pharmaceutically acceptable carrier or diluent.

Another object of this invention is to provide a method of determining the capacity of a drug to modulate expression, production, or formation of amyloid precursor protein (APP) in an eukaryotic cell comprising, contacting a drug with an eukaryotic cell containing estrogen receptors.

Yet another object of this invention is to provide compositions and methods for alleviating the negative effects of a neurological disorder or neurodegenerative disease stemming from the aberrant expression, production, formation, or overexpression of amyloid precursor protein (APP) in a subject, comprising administering to a subject suffering from the above-noted disorder or disease an effective amount of a lipophilic hormone, and a pharmaceutically suitable carrier or diluent.

Consistent with the objectives of this invention, a method of modulating APP is provided which comprises administering to a subject in need of treatment an effective amount of a substance that regulates APP promoter activity, and other activities related to APP gene transcription and translation. Other embodiments includes methods of treating and alleviating neurodegenerative or cognitive changes in postmenopausal women, comprising administering to a woman in need of treatment an effective amount of an estrogenic compound.

DETAILED DESCRIPTION OF THE PREFERRED EMBODIMENTS

The inventors have shown that APP expression can be regulated by lipophilic hormones that interact with cytosolic or nuclear receptors.

In this study, confluent primary rat cortical neurons, astrocytes, or human glioma cells (HS683), which were treated over a 24 hour period with 1, 10, or 100 μM of a lipophilic estrogenic compound, such as estrone or 17β-estradiol, gave rise to decreased levels of cellular APP, compared to those levels that are observed in untreated control cells. See, e.g., FIGS. 1, 2, and 3. The levels of APP holoprotein associated with cultured brain cells (e.g. astrocytes or neurons) and HS683 cells were measured with an antisera R37 (gift of Dr. F. Kametani, Tokyo Inst. of Psychiatry) or with monoclonal antibody 22C11 (BoehringerMannheim) directed against the C-terminus or N-terminus of APP, respectively, using Western blot analyses. The total cell protein content as measured by the bicinchoninic acid assay was not changed by these estrogenic compounds in the range of concentrations tested.

Figure 1:
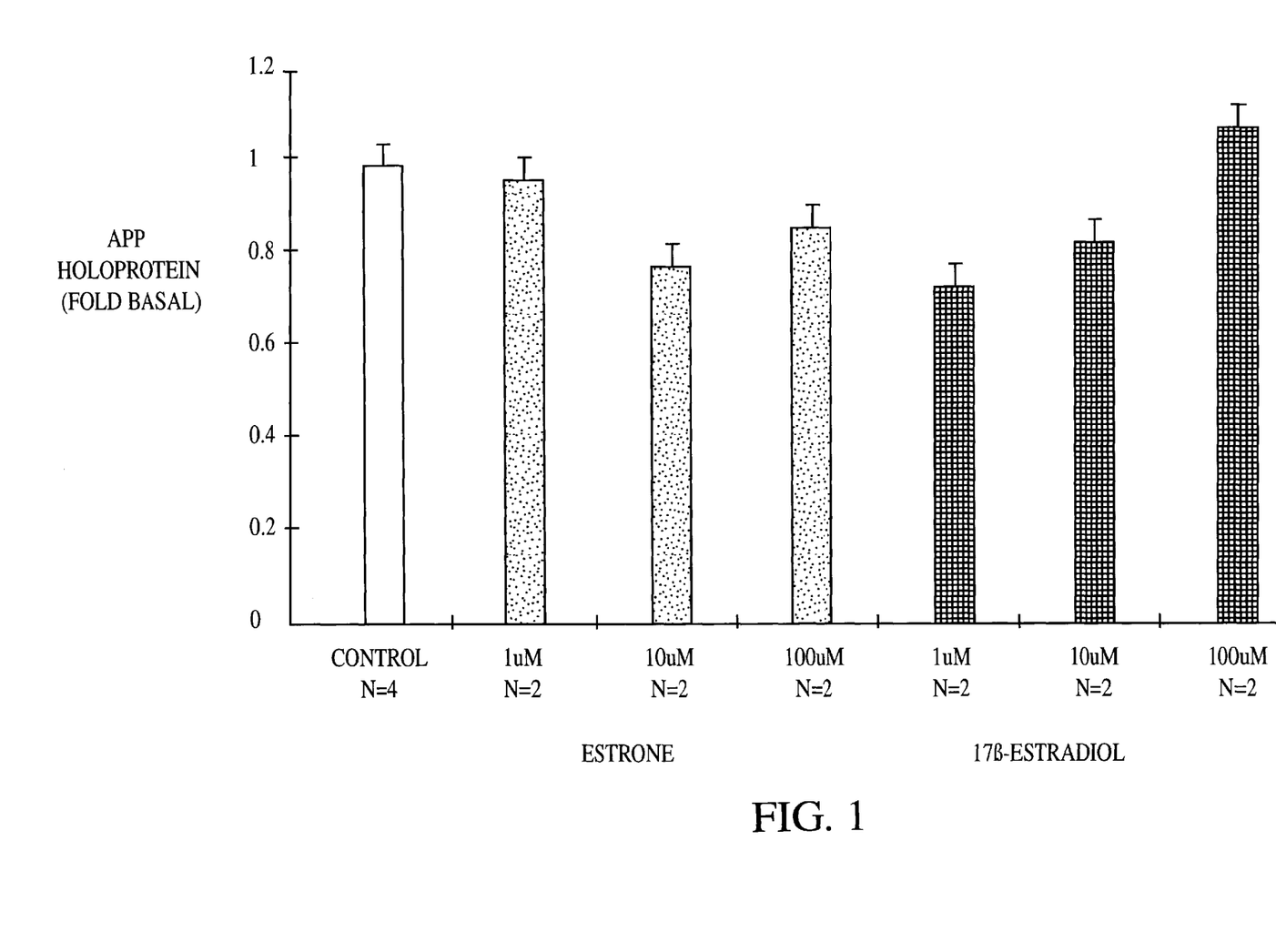
FIG. 1 illustrates the effects of estrone and 17β-estradiol on APP holoprotein synthesis in confluent primary rat cortical neurons.
Figure 2:
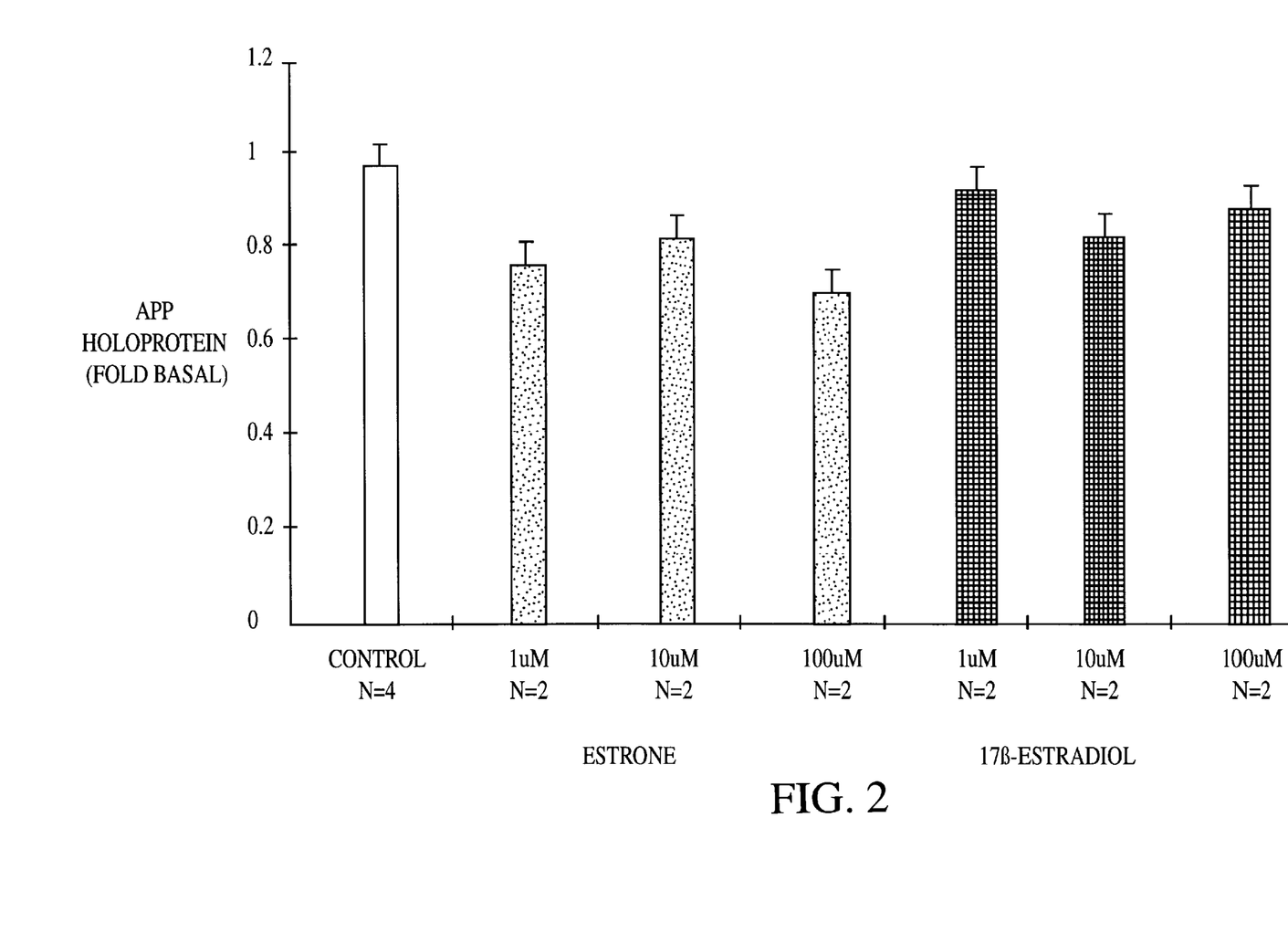
FIG. 2 illustrates the effects of estrone and 17β-estradiol on APP holoprotein synthesis in confluent primary rat cortical astrocytes.
Figure 3:
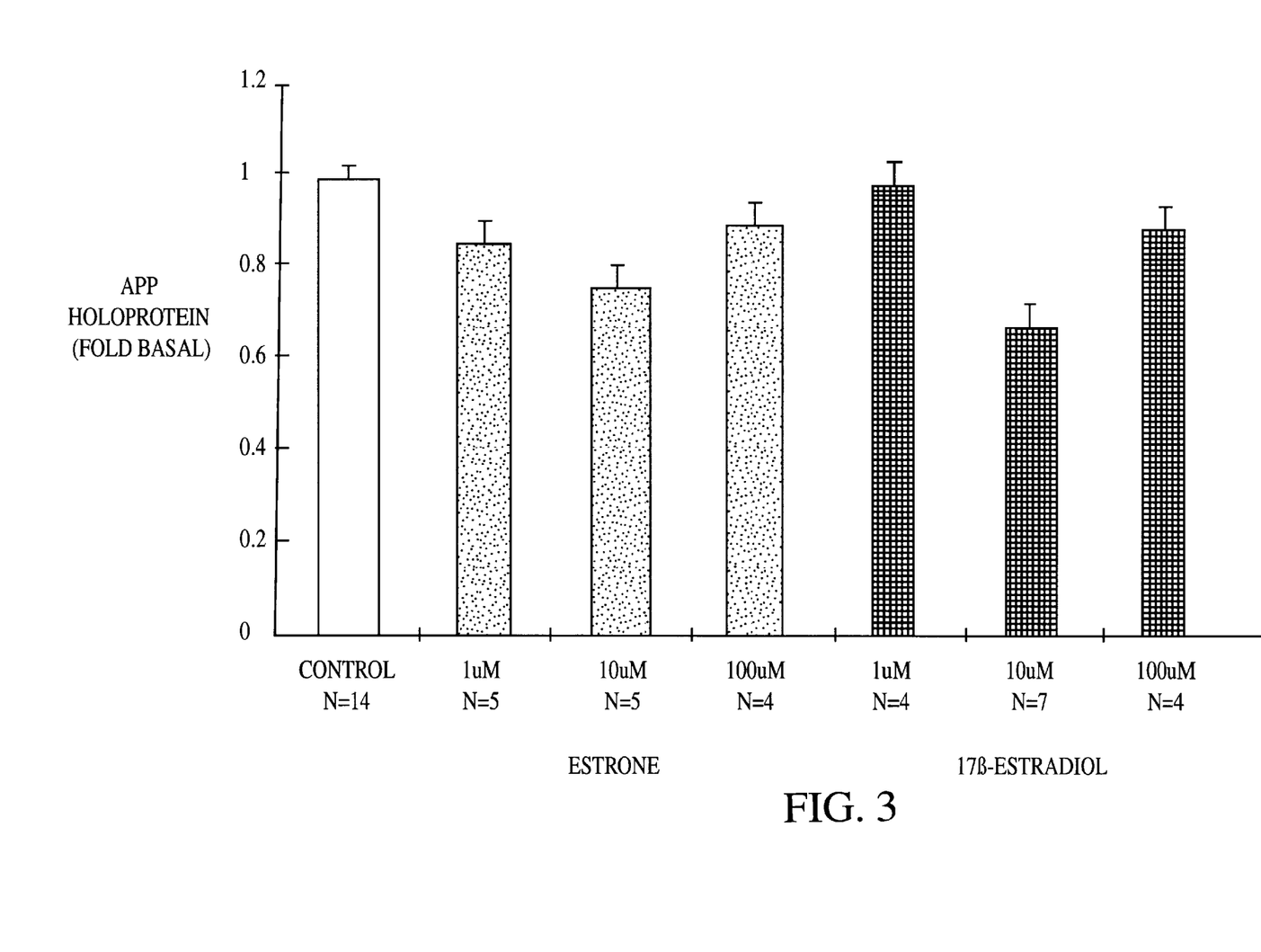
FIG. 3 illustrates the effects of estrone and 17β-estradiol on APP holoprotein synthesis in human glioma cells (HS683).

These data suggests that estrogenic compounds reduce APP holoprotein levels by decreasing APP synthesis. The decrease in the level of APP synthesis is specially pronounced with 10 μM estrone in cultured neurons and HS683 cells, and 10 μM 17β-estradiol in cultured HS638 cells. The reduction in APP holoprotein caused by 17β-estradiol or estrone is also expected to reduce neurotoxicity or neurodegeneration associated with APP over expression.

Additionally, these results suggests that the mechanisms regulating APP synthesis or metabolism may differ among different types of cells. LeBlanc, A. C. *J. Neurochem.*2300, (1996); and LeBlanc. A. C. *J. Neurochem.* 1183 (1997) disclose that the level of amyloidogenic processing of APP differs among brain cells such as neurons, astrocytes and microglia. These authors concluded that human neurons and astrocytes generate higher levels of amyloidogenic fragments than microglia.

Jaffe et al. *J. Biolo. Chem.*269, 13065 (1994) disclose the possible effect of estrogen on the metabolism of the Alzheimer's amyloid precursor protein (APP). Using the breast carcinoma cell line, these authors found that treatment with physiological concentrations of 17β-estradiol is associated with extracellular accumulation of soluble APP (APPs). However, these authors found no changes in the levels of intracellular immature or mature APP holoproteins, suggesting that estrogen may increase the secretory metabolism of APP.

In contrast to Jaffe et al., our data, using brain cells, demonstrate a decrease in the level of intracellular APP holoprotein with administration of estrogenic compounds. The lower concentration of estradiol and the use of breast carcinoma cells by Jaffe et al may account for Jaffe et al's inability to detect a decrease in the level of APP holoprotein. There are functional differences between breast carcinoma cells and brain cells. The mechanisms regulating APP synthesis and metabolism between carcinoma/cancer cells and bona fide brain cells (e.g., neurons, astrocytes) are likely to be different (see, Mills and Reiner, *J. Neurochem.* 67, 1511 (1996)).

The decrease in APP holoprotein levels, as disclosed herein, is associated with decreased production of APP mRNA, or decreased translation of mRNA to produce APP holoprotein. Northern blots are used to determine the levels of APP mRNA in the absence or presence of estrone or 17β-estradiol. The results suggests a decrease in the level of APP mRNA in the presence of these compounds. Also, Western blot analysis and inhibitors of transcription (e.g., actinomycin D) or translation (e.g., cycloheximide) are used to measure the levels of APP holoprotein in cells treated with estrogenic compounds. Again, a decrease in the level of APP holoprotein is found to be associated with the administration of the estrogenic compounds.

Estrogenic compounds are known to uncouple g-proteins. Since cell-surface receptors activate g-proteins in order to regulate intracellular signaling pathways, estrogenic compounds may also regulate signaling pathways that regulate APP synthesis and metabolism. For instance, activation of cell-surface receptors coupled to cAMP stimulates increases in amyloidogenic APP holoprotein. Uncoupling g-proteins by estrogenic compounds may reduce cAMP production and thus, prevent the formation of amyloidogenic APP holoprotein.

Previously, we have shown that stimulation of certain cell-surface receptors coupled to cAMP formation in astrocytes increases the production of APP mRNA and APP holoprotein. It is suggested that the up regulation or aberrant activation of certain receptors in brain regions that are vulnerable to damage can stimulate APP overexpression in brain cells and, thereby, contribute to amyloid production. Because APP over expression can cause neurodegeneration and cognitive dysfunction, the inventors have shown that such substances as neuroactive steroids and related products, e.g., estrone and 17β-estradiol and the like, are promising drug candidates for the treatment of Alzheimer's, Parkinson's, Lou Gehrig's Disease (amylotrophic lateral sclerosis), multiple sclerosis, ischemia, traumatic brain injury, epileptic seizure, and the like, which may have their roots in the formation or presence of amyloid plaques.

Accordingly, it is an object of the present invention to provide methods and compositions that modulate or regulate the production or formation of APP in patients, including the expression of APP gene products and the transcription or translation of the APP gene in brain cells. For example, the production of APP by mammalian cells, in particular, by cells in the brain, can be increased or reduced.

In attaining this objective, it is also an objective of the invention to inhibit excessive APP holoprotein formation, prevent neural dystrophy and alleviate pathological symptoms, such as neurodegeneration or cognitive deficits that may arise from the negative effects of inappropriately expressed, produced, or formed amounts of APP.

FURTHER ASPECTS OF THE PREFERRED EMBODIMENTS

Thus, the present invention is directed to a method of modulating the expression, production, or formation of amyloid precursor protein (APP) in a subject comprising administering to the subject an effective amount of a lipophilic hormone, such as estrone or 17β-pestradiol, an analog of a lipophilic hormone, a substance that is a ligand, an agonist, or an antagonist of a receptor that is coupled to a lipophilic hormone, or a compound that regulates the activity of cytosolic or nuclear receptors. In specific embodiments of the invention the lipophilic hormones and related compounds comprise; Allopregnanolone; Allotetrahydrodeoxycorticosterone; Alphaxalone; Androsterone, 4-Androstane-3,17-dione, Corticosterone; Corticosterone: HBC complex; Danazol; Dehydroepiandrosterone sulfate sodium; Dexamethasone; 17β-Estradiol; 17β-Estradiol: HBC complex; Estrone; Etiocholanolone; FGIN I-27; Fluoxymesterone; Hydrocortisone; Hydrocortisone: HBC complex; Methandrostenolone; Nandrolone decanoate; Oxandrolone; Oxymetholone; Prednisolone; Pregnenolone sulfate sodium; Progesterone; Progesterone: HBC complex; Spironolactone; Stanolone; Tamoxifen; 3-hydroxy; citrate; (E)-; Tamoxifen, 4-hydroxy-, (E)-; Tamoxifen, 4-hydroxy-, (Z)-; Testosterone: HBC complex; Testosterone, 17β-cypionate; Testosterone, 17β-decanoate; Testosterone, 17β-heptanoate; Testosterone, 17β-isocapronate; Testosterone, 17α-methyl-; Testosterone, 17β-propionate; Triamcinolope; U-73122; U-73343; Endosulfan; dieldrin; methoxychlor; thyroid hormones; nethimazole (antithyroid hormones); human growth hormones; gonadotropin; vasopressin; calcitonin; adrenal cortical hormones; insulin; anabolic steroids; and antineoplastics.

By "APP overexpression" is meant any activity that is exerted in the nucleus of a eukaryotic cell that ultimately gives rise to expression, production, or formation of APP in a subject, including but not limited to the regulation of the promoter of the APP gene, the modulation of APP metabolism transcriptional factors that affect APP expression, or the stimulation of the activity of second messengers.

Indeed, according to the methods of the present invention, a suitable antagonist can comprise a receptor antagonist of a neurotransmitter, an antagonist of a lipophilic hormone, and the like. Examples of additional substances, which have been found to decrease or inhibit the APP synthesis include, but are not limited to H8, H9, cyclosporin A, FK-506, Win55212, and propranolol.

When it is desirable to effect a decrease of endogenous APP production, cellular levels of cAMP are caused to diminish. For example, the cellular levels of cAMP can be decreased by retarding the production of endogenous cAMP or by stimulating the breakdown of cAMP. Substances, such as H8, H9, propranolol, or Win55212 can be administered to achieve this end.

An important aspect of the present invention concerns the treatment of a subject that has suffered an injury or trauma, especially to the head or brain, or of a subject that is, for some other or related reason, may be experiencing over-stimulation of cAMP expression, production, formation (or, collectively, "synthesis").

It is particularly advantageous to treat the subject in need by administering an effective amount of a lipophilic hormone such as estrone or 17β-estradiol. It is noteworthy that the present invention is also directed to a method of determining the capacity of a drug to inhibit the expression, production, or formation of amyloid precursor protein (APP) in a cell comprising contacting an estrogenic drug, an analog of an estrogenic drug, a substance that is a ligand, an agonist, or an antagonist of an estrogen receptor, with a cell culture that has the capacity to synthesize APP holoprotein. The level of APP mRNA or holoprotein produced from the cell culture in the presence of the drug is then compared with the level of APP mRNA or holoprotein produced from the cell culture in the absence of the drug. The cell can be any type of microbial, plant, or animal cell, so long as the cell has the capacity to express, produce, or otherwise form APP. The cell is preferably an eukaryotic cell. More preferably, the eukaryotic cell can further be a yeast cell, insect cell, invertebrate, vertebrate, or mammalian, including animal or human.

It should be apparent that the present invention is directed to a method of alleviating the negative effects of a neurological disorder or neurodegenerative disease stemming from the aberrant expression, production, or formation of amyloid precursor protein (APP) in a subject. In a particular embodiment, an effective amount of a lipophilic hormone such as estrone or 17β-estradiol, or an analog or agonist thereof, is administered to the subject suffering from the disorder or disease. As described herein, the present method of modulating amyloid precursor protein (APP) expression in a subject may also comprise administering to the subject an effective amount of a substance that regulates APP promoter activity, either by stimulating APP promoter activity or retarding it.

The inhibition of APP promoter activity can, in turn, regulate the expression of abnormal forms of tau. And, hence, the present invention also contemplates a method of regulating the expression of abnormal forms of tau in a subject comprising modulating amyloid precursor protein (APP) expression in the subject.

Moreover, compositions for modulating the expression, production, or formation of amyloid precursor protein (APP) in a subject are intended which comprise neuroactive steroids, such as estrone or 17β-estradiol, analogs of neuroactive steroids, a substance that is a ligand, an agonist, or an antagonist of a receptor that is coupled to a neuroactive steroid, or a compound that regulates the activity of cytosolic or nuclear receptors.

COMPOSITIONS OF THE PRESENT INVENTION

As should be apparent, the present invention also contemplates compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laureate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

By a "therapeutically effective amount" or simply "effective amount" of an active compound, such as an analog of estrogen, is meant a sufficient amount of the compound to treat or alleviate the negative effects of a neurological disorder or neurodegenerative disease stemming from an increase in the level of expression, production, or formation of amyloid precursor protein (APP) at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts thereof to make up the daily dose. In general, treatment regimens according to the present invention comprise administration to a human or other mammal in need of such treatment from about 1 mg to about 1000 mg of the active substances of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours.

The compounds of the present invention may be administered alone or, in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrixes of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable nonirritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gel caps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hardfilled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Accordingly, the present invention is useful in the treatment or alleviation of disease, especially those disorders related to neurological diseases or neurodegenerative disorders, such as Alzheimer's disease, Parkinson's disease, Lou Gehrig's disease, multiple sclerosis, central or peripheral nervous system damage, dysfunction, or complications involving same stemming from edema, injury, or trauma, or neurodegenerative changes in postmenopausal women. Such damage, dysfunction, or complications may be characterized by an apparent neurological, neurodegenerative, physiological, psychological, or behavioral aberrations, the symptoms of which can be reduced by the administration of an effective amount of the active compounds or substances of the present invention.

The following examples are provided for further illustration of the present invention, and do not limit the invention.

EXAMPLES

Experiments and exemplary procedures are described below which provide additional enabling support for the present invention. In particular, in vitro studies using primary cultures of rat cortical astrocytes and human glioma cells are disclosed.

General Methods

Neurons and astrocytes are isolated from cortices from embryonic and postnatal rats, respectively. See, K. D. McCarthy and J. de Vellis, *J. Cell Biol.* 85, 890 (1980). In brief, dissected cortices were dissociated by trypsinization and trituration through a flame-polished Pasteur pipette. Cells were plated onto poly-L-lysine coated 35- or 100 mm culture dishes at densities of about 10–25 cells/mm$^2$. The initial, culture media, minimal essential medium (MEM, Gibco) containing 10% horse serum (BioWhittaker), were aspirated after 2–5 h after plating to remove unattached cells and debris, and replaced with MEM containing 7.5% fetal bovine serum (FBS, BioWhittaker). Half the media was replaced with MEM/7.5% FBS twice weekly. Cells are kept at 37° C. in a humidified 5% $CO_2$/95% air incubator. Media are changed twice weekly. Immunocytochemical staining with antibodies against GFAP and tau shows that >90% of cultured cells are astrocytes and <5% are neurons. Pharmacological manipulations are performed in serum-free media on 7–14 DIV confluent astrocytes.

Detection of Cell-Associated Protein

To detect cell-associated protein (APP or GFAP) astrocytes from 35 mm dishes are scraped in lysis buffer (60 mM Tris/HC1, 4% SDS, 20% glycerol, 1 mM dithiothreitol), ultrasonicated and boiled for 5 min. The total amount of cell protein per dish, estimated using the bicinchoninic acid assay, is not altered by pharmacological treatments. Bromphenol blue (0.1%) is added to each sample and equal amounts of protein (~75 mg/lane) are loaded on 10% SDS-polyacrylamide gels.

To detect secreted APP, culture media was collected after drug treatments and phenylmethylsulfonyl fluoride was added to a final concentration of 2 mM. The media samples were then applied to Sephadex PD-10 desalting columns (Pharmacia) and eluted with distilled water. Column eluates were frozen and dried by vacuum centrifugation. The lyophilized proteins were reconstituted in 25 µL water followed by 25 µL of 2×Laemmli gel loading buffer, and boiled for 5 min.

The amount of media or cell protein loaded for sodium dodecyl sulfate-polyacrylamide gel electrophoresis (10–20% SDS PAGE; Bio-Rad) was Formalized for the amount of protein per sample. Proteins (equivalent to ~100 µg cell protein/lane) were separated by electrophoresis, electroblotted onto polyvinylidene difluoride membranes (Immobilon-P, Millipore) and blocked in Tris-buffered saline with 0.15% Tween 20 (TBST) containing 5% powdered milk for 30 min. After 2×10 min rinses in TBST, the membranes were incubated in TBST containing an appropriate antibody. Monoclonal antibodies 22Cll and GFAP (both from Boehringer-Mannheim) were used to detect the N-terminus of A. P. and glial fibrillary acidic protein respectively; antisera R37 and R98 (gifts of Dr. F. Kametani, Tokyo Institute of Psychiatry) were used to detected the C-terminus and KPI motifs of APP, respectively; antiserum C8 (gift of Dr. D. Selkoe, Women's Hospital, Harvard Medical School, Cambridge, Mass.) was used to detect the C-terminus of APP.

After an overnight incubation, membranes were rinsed in TBST before being treated for 1h with a peroxidase-linked secondary antibody. After several rinses in TBST, protein bands were visualized on Kodak X-AR films by an enhanced chemiluminescence method (Amersham). Optical densities of the protein bands were quantitated by laser scanning densitometry (LKB, Bromma, Sweden), and normalized to the densities of those bands generated under control conditions.

cAMP Assay

Levels of cyclic AMP were measured with [8-$^3$H]- cAMP assay kit (Amersham TRK 432) in astrocytes grown on 35 mm dishes. In brief, after aspirating the medium and rinsing twice with 1 ml ice cold PBS, the cells were scraped in 0.8 ml ice cold ethanol and sonicated. The cell suspension was incubated for 5 min at room temperature, centrifuged and the supernatant was dried in a rotary evaporator. After resuspension in 120 μl Tris/EDTA buffer, two duplicate samples of 50 μl each were mixed with the binding protein, [8-$^3$H] adenosine 3', 5'-cyclic phosphate tracer and incubated at 2–4° C. for 2 h. A charcoal suspension (100 μl) was added to the samples before centrifugation and 200 μl of the supernatant were removed for scintillation counting. The amount of cyclic AMP (pmol/mg protein) was estimated by comparing to known standards, and normalized to the amounts of whole cell protein as determined by the bicinchoninic acid assay (Sigma).

Data Analysis

Measurements of cellular and secreted proteins, or of mRNA in treatment groups were normalized against those of control groups which were prepared in parallel and loaded onto the same blot. Analysis of variance (ANOVA) and t-tests were used to evaluate differences between groups (significance level, p=0.05), using drug treatments as the independent variable.

Analysis of RNA

Total RNA from astrocytes grown on 100 mm dishes is extracted by the acid guanidium thiocyanate-phenolchloroform method. See, P. Chomcznski and N. Saachi, *Anal. Biochem.* 162, 156 (1987). In brief, the medium was aspirated and the cells were scraped in 1 mL of TRI Reagent. After incubation for 15 min at room temperature, 0.2 ml chloroform was added, mixed vigorously with TRI Reagent and the mixture was stored for another 15 min at room temperature. After centrifugation at 12,000 g for 15 min, 0.5 ml isopropanol was added to the aqueous phase of the mixture to precipitate RNA. The RNA pellet collected by centrifugation (12,000 g, 15 min at 4° C.) was washed with 70% ethanol once and solubilized in an appropriate amount of Formazol (Molecular Research Center, Cincinnati, Ohio). RNA samples (–20 μg) were denatured by heating for 15 min at 60° C. prior to loading onto 1.2% agarose-formaldehyde gels for electrophoresis.

RNA was blotted onto Hybond polyvinyl membranes by overnight capillary transfer and fixed onto the membranes by UV light illumination. Membranes were pre-hybridized with Amersham Rapid-hyb (Amersham Lab, Arlington Heights, Ill.) buffer for 2 h and labeled overnight with a ~1.8 kb human APP cDNA (gift of Dr. Rachael Neve, McLean Hospital, Harvard Medical School, Belmont, Mass.) or human glyceraldehyde-3-phosphate dehydrogenase probe (G3PDH; Clontech) labeled with ($^{32}$P]DCTP using random primed extension (Amersham Megaprime DNA labeling kit). Membranes were dried and exposed to Kodak X-ray film for 24–48 h with an Amersham enhancer sheet. The relative amounts of mRNA obtained by hybridization were estimated using densitometric analysis of autoradiographs. The levels of APP mRNA were normalized to the amounts of G3PDH mRNA and expressed as a ratio to the levels of untreated, control cells.

Exposure of Astrocytes, Neurons, and Human Glioma Cells to Lipophilic Estrogenic Compounds Confluent monolayers primary rat cortical neurons, astrocytes- prepared according to Example 5.1- and human glioma cells (HS683) were treated over 24 hours with 1, 10, or 100 μM of a lipophilic estrogenic compounds, such as estrone or 17β-estradiol. The result shows a decrease in the level of APP holoprotein synthesis in the brain cells treated with lipophilic estrogenic compounds, as compared to those levels that are observed in untreated, control cells. See, e.g., FIGS. 1, 2, and 3. The levels of APP holoprotein associated with cultured brain cells (e.g. astrocytes or neurons) and HS683 cells were measured with an antisera R37 (gift of Dr. F. Kametani, Tokyo Inst. of Psychiatry) or with monoclonal antibody 22C11 (Boehringer-Mannheim) directed against the C-terminus or N-terminus of APP, respectively. Using Western blot analysis, it is found that the total cell protein content as measured by the bicinchoninic acid assay was not changed by these estrogenic compounds in the range of concentrations tested.

In Vivo Studies

The present studies indicate that lipophilic hormones that interact with cytosolic or nuclear receptors reduce the level of APP holoprotein synthesis in rats and human's brain cells. Reactive astrocytes (that is, astrocytes that have been activated or stimulated in some fashion, e.g., those associated with brain or neuronal injury) in vivo also up regulate GFAP expression. Indeed, the examination of post-mortem brains in patients with Alzheimer's disease shows that reactive astrocytes are found in proximity to amyloid plaques and regions of neurodegeneration. The inventors believe that neuronal, brain, or head injury gives rise to the formation of reactive astrocytes, which over express APP and contribute to the formation of amyloid or neurotoxic APP derivatives.

Thus, animal models of head injury and Alzheimer's disease exhibit increased amounts of APP in the brain. The in vivo administration of a lipophilic hormone, like estrone, is found to inhibit APP overexpression and the associated neurological disorders. Inasmuch as estrogen deficiency in postmenopausal women is associated with a higher incidence of Alzheimer's disease, this discovery opens the possibility that estrogen therapy may prevent some of the neurodegenerative and cognitive changes associated with postmenopausal women, Alzheimer's disease, aging and other disease conditions associated with such neurodegenerative and cognitive decline.

CONCLUSION

Accordingly, the invention provides compositions and methods for preventing, alleviating, or inhibiting abnormal APP synthesis, or reducing APP expression, by the administration of lipophilic hormones that interact with cytosolic or nuclear receptors. Particularly where the upregulation of such receptors and APP overexpression accompanies brain trauma, neurological disease, or neurodegenerative disorder.

Hence, the invention provides relief from the neuropathological symptoms of diseases, such as Alzheimer's disease, or postmenopausal neurodegenerative or cognitive syndromes by inhibiting aberrant APP gene expression, and reducing the level of APP holoprotein synthesis. It is the overexpression of APP that is believed to cause or strongly contribute to neurodegeneration and cognitive dysfunction in animals and humans.

It should be apparent to those of ordinary skill that the discussion presented herein adequately supports the hypothesis that a reduction in APP synthesis (as evidenced by decrease in APP DNA transcription and translation) can be achieved by regulating cytosolic or nuclear receptors.

It should also be apparent that other embodiments of the invention can be readily contemplated by those of ordinary skill in the art after reviewing the present specification and teachings. The present invention is not limited, however, to the specific embodiments presented herein and should not be construed so narrowly as to exclude embodiments that fall within the scope and spirit of the invention, which invention is limited solely by the following claims.

What is claimed is:

1. A method of inhibiting expression, production, or formation of amyloid precursor protein (APP) in a subject comprising administering to the subject an effective amount of an agent wherein said agent is a lipophilic hormone, anaalog of a lipophilic hormone, a substance that is a ligand, an agonist, or an antagonist of a receptor that is coupled to a lipophilic hormone, and a pharmaceutically acceptable carrier or diluent, in which the effective amount is at least about 0.20 mg/kg body weight, and wherein said agent is selected from the group consisting of androsterone; 4-androstane-3,17-dione; danazol; dehydroepiandrosterone sulfate sodium; estradiol; 17β-estradiol; 17β-estradiol; HBC complex; estrone; fluoxymesterone; methandrostenolone; nandrolone decanoate; oxandrolone; oxymetholone; pregnenolone sulfate sodium; progesterone; progesterone; HBC complex; stanolone; testosterone; HBC complex; testosterone, 17β-cypionate; testosterone, 17β-decanoate; testosterone, 17β-heptanoate; testosterone, 17β-isocapronate; testosterone, 17α-methyl-; testosterone, 17β-propianate; methoxychlor; and gonadotropin.

2. The method of claim 1 in which APP is overexpressed.

3. The method of claim 2 in which overexpression is affected by alteration in signal transduction mechanism or receptor activation.

4. The method of claim 1 in which the subject is exposed to effective amounts of a lipophilic hormone for a continuous period of about 24 hours.

5. The method of claim 1 in which APP expression is diminished by inhibiting the transcription of APP DNA or translation of APP mRNA.

6. A method of determining the capacity of a drug to inhibit expression, production, or formation of amyloid precursor protein (APP) in an eukaryotic cell comprising:

(i) contacting a drug with an eukaryotic cell containing estrogen receptors, (ii) comparing the level of APP mRNA or holoprotein produced from said eukaryotic cell culture in the presence of said drug with the level of APP mRNA produced from said eukaryotic cell culture in the absence of said drug.

7. The method of claim 6, wherein the total cell protein content is not changed by said drug.

8. The method of claim 6 in which said drug is a lipophilic hormone, an analog of a lipophilic hormone, a substance that is a ligand, an agonist, or an antagonist of a receptor that is coupled to a lipophilic hormone.

9. A method of alleviating the negative effects of a neurological disorder or neurodegenerative disease stemming from the abberant expression, production, formation, or overexpression of amyloid precursor protein (APP) in a subject, comprising administering to a subject suffering from said disorder or disease an effective amount of an agent wherein said agent is a lipophilic hormone, an analog of a lipophilic hormone, a substance that is a ligand, an agonist, or an antagonist of a receptor that is coupled to a lipophilic hormone, and a pharmaceutically acceptable carrier or diluent, in which the effective amount is at least about 0.20 mg/kg body weight, and wherein said agent is selected from the group consisting of androsterone; 4-androstane-3,17-dione; danazol; dehydroepiandrosterone sulfate sodium; estradiol; 17β-estradiol; 17β-estradiol; HBC complex; estrone; fluoxymesterone; methandrostenolone; nandrolone; decanoate; oxandrolone; oxymetholone; pregnenolone sulfate sodium; progesterone; progesterone; HBC complex; stanolone; testosterone; HBC complex; testosterone, 17β-cypionate; testosterone, 17β-decanoate; testosterone, 17β-heptanoate; testosterone, 17β-isocapronate; testosterone, 17α-methyl-; testosterone, 17β-propionate; methoxychlor; and gonadotropin.

10. The method of claim 9 in which said neurological disorder is a postmenopausal disorder.

11. The method of claim 9 in which said neurodegenerative disease is Alzheimer's disease.

12. The method of claim 9 in which the antagonist of a lipophilic hormone is selected from the group consisting of H8, H9, cyclosporin A, FK-506, Win 55212, and propanolol.

13. The method of claim 9 in which the neurological disorder or neurodegenerative disease is selected from the group consisting of Alzheimer's disease; Parkinson's disease; Lou Gehrig's disease; multiple sclerosis; central or peripheral nervous system damage, dysfunction, or complications involving same stemming from edema, injury, or trauma; and neurodegenerative changes in postmenopausal women.

* * * * *